US00PP13325P2

(12) United States Plant Patent
Olesen et al.

(10) Patent No.: US PP13,325 P2
(45) Date of Patent: Dec. 10, 2002

(54) MINIATURE ROSE PLANT NAMED 'POULUSH'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 202 days.

(21) Appl. No.: 09/662,285

(22) Filed: Sep. 14, 2000

(51) Int. Cl.[7] ..... A01H 5/00
(52) U.S. Cl. ..... Plt./119
(58) Field of Search ..... Plt./116, 119, 121

(56) References Cited

PUBLICATIONS

Community Plant Variety Office, "Certificate on the Grant of Community Plant Variety Rights" Oct. 2, 2000. 6 pages. EU. UPOV–ROM, 2001/03, Plant Variety Database, GTI Jouve Retrieval software, 2 citations for 'POULush'.*

* cited by examiner

*Primary Examiner*—Howard J. Locker

(57) ABSTRACT

A new miniature rose plant which has abundant flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of miniature rose plant which originated from a controlled crossing between an unnamed seedling and an unnamed seedling. The two parents were crossed and the resulting seeds were planted in a controlled environment. The new variety is named 'POULush'.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which made a variety suitable for distribution in the floral industry.

This combination of qualities is not present in previously available commercial cultivars of this type and distinguish 'POULush' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULush' was selected by the inventors as a single plant from the progeny of the hybridization in Fredensborg, Denmark.

Asexual reproduction of 'POULush' by cuttings and traditional budding onto *Rosa multiflora* understock was first done by L. Pernille and Mogens N. Olesen in Fredensborg, Denmark. This initial and other subsequent propagations conducted in controlled environments have demonstrated that the characteristics of 'POULush' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULush'. Specifically illustrated in SHEET 1:

1. Stem showing branches and the attachment of leaves, buds, and peduncles;
2. Flower bud, partially opened bud, and open bloom;
3. Flower petals, detached;
4. Sepals, receptacle, and pedicel;
5. Two stems, one bare, exhibiting thorns;
6. Leaves.

DETAILED DESCRIPTION OF THE VARIETY

The following is a description of 'POULush' as observed in its growth in in glasshouses in Half Moon Bay, Calif. Color references are made using The Royal Horticultural Society (London, England) Colour Chart, 1995, except where common terms of color are used.

For a comparison, several physical characteristics of the rose variety 'POULrael', a rose variety from the same inventors described and illustrated in U.S. Plant Pat. No. 11,499, and issued on Sep. 5, 2000, are compared to 'POULush' in Chart 1.

CHART 1

| | 'POULush' | 'POULrael' |
|---|---|---|
| Bud Color at 1/4 open | Orange Group 24D | Yellow-White Group 158D |
| Upon opening, color of upper surface of petal | Outermost petals: Orange Group 27D. Innermost Petals: Orange Group 27D. | Outermost petals: Orange Goup 27D. Innermost Petals: Red Group 36A. |
| Basal petal spot | Outermost petals: White Group 155C. Innermost Petals: White Group 155C. | Outermost petals: Yellow Group 4B–4C. Innermost Petals: Yellow Group 4A. |

Parents: Unnamed seedling×Unnamed seedling.
Classification:
*Botanical.*—*Rosa hybrida.*
*Commercial.*—Miniature.

FLOWER AND FLOWER BUD

Blooming habit

Flower bud:

*Size.*—Upon opening, 13 mm.–15 mm in length from base of receptacle to end of bud.

*Bud form.*—Short and globular.

*Bud color.*—As sepals unfold, Orange Group 24D; Orange Group 24D at ¼ opening.

*Sepals.*—Green Group 137C. Moderate foliaceous appendages on 3 or the 5 sepals. Surfaces of sepals very moderately pubescent. Stipitate glands are present in limited quantities on edges of sepals.

*Receptacle.*—Surface: Smooth. Shape: Funnel-shaped. Size: 3 mm(h)×4 mm (w). Color: Yellow-Green Group 144A.

*Peduncle.*—Surface: Smooth with limited quantities of stipitate glands. Length: 15 to 20 mm average length. Color: Yellow-Green Group 144B–C. Strength: Upright.

*Borne.*—Generally with 4 to 5 buds per flowering stem.

Flower bloom:

*Fragrance.*—Light.

*Duration.*—As a pot plant, flowers last from 8 to 10 days. As a cut flower 4 to 6 days.

*Size.*—Large for an 10 cm pot rose. Average flower diameter is 35 mm when open.

*Form.*—Shape of flower when viewed from the side: Upon opening, upper part: Cupped. Upon opening, lower part: Flattened convex . Open flower, upper part: Flattened convex. Open flower, lower part: Concave.

*Petalage.*—Average range: 45–55 petals under normal conditions with 2 to 3 petaloids.

Color:

*Upon opening, petals.*—Outermost petals: Upper Surface: Orange Group 27D. Reverse Side: Red Group 36D. Innermost petals: Upper Surface: Orange Group 27D. Reverse Side: Orange Group 29D.

*Upon opening, basal petal spots.*—Outermost petals: Outer Side: White Group 155C. Inner Side: White Group 155C. Innermost petals: Outer Side: White Group 155C. Inner Side: White Group 155C.

*After opening, petals.*—Outermost petals: Outer Side: Orange Group 27D. Inner Side: Orange Group 27D. Innermost petals: Outer Side: Red Group 36C. Inner Side: Red Grou 38D.

*After opening, basal petal spots.*—Outermost petals: Outer Side: White Group 155C. Inner Side: White Group 155C. Innermost petals: Outer Side: White Group 155C. Inner Side: White Group 155C.

General tonality: On open flower, Orange Group 29C–D. No change in the general tonality at the end of the $12^{th}$ day. Afterwards, general tonality is Orange Group 27D.

Petals:

*Petal reflex.*—Petals are strongly reflexed.

*Petal edge.*—Pointed in center of margin.

*Shape.*—Deltoid.

*Petaloids.*—2 to 3 present.

*Thickness.*—Thick.

*Arrangement.*—Imbricated.

Reproductive organs:

*Pollen.*—Color: Greyed-Orange Group 163A. Abundance: Limited.

*Anthers.*—Size: Small. Color: White Group 155C. Abundance: Limited.

*Filaments.*—Color: Yellow Group 5A–B.

*Stigmas.*—Slightly superior in location to anthers. Color: Greyed-Yellow Group 160D.

*Styles.*—Color: Yellow-Green Group 145C–D.

*Seed formation.*—Hips not observed on pot plants.

PLANT

Plant growth: Vigorous, compact, upright to bushy. When grown in a 10 cm pot (as is typical in the commercial production of the variety), the average height of the plant is 18 to 20 cm and the average width is 20 to 25 cm.

Stems:

*Color.*—Young wood: Yellow-Green Group 144A. Older wood: Yellow-Green Group 144A.

*Prickles.*—Incidence: Moderate. Size: Average length: 3 mm–4 mm. Color: Greyed-Yellow Group 163C. Shape: Linear.

*Surface.*—Young wood: Smooth. Older wood: Smooth.

Plant foliage: Normal number of leaflets on normal leaves in middle of the stem: 5 leaflets.

*Leaf size.*—20 mm (l)×14 mm (w).

*Abundance.*—Average.

*Color.*—Upper Leaf Surface: Green Group 139A. Lower Leaf Surface: Yellow-Green Group 147B. Juvenile foliage: Upper Leaf Surface: Green Group 137B. Lower Leaf Surface: Green Group 138A.

Plant leaves and leaflets:

*Stipules.*—Size: 8 mm–12 mm. Color: Green Group 137A. Stipitate glands present in limited quantities on edges of stipules.

*Petiole.*—Length: 10 mm–12 mm. Color: Green Group 137A. Underneath: Yellow-Green Group 144A. Margins: Green Group 137A.

*Rachis.*—Color: Green Group 134A. Underneath: Yellow-Green Group 144A. Margins: Green Group 137A.

*Leaflet.*—Edge: Serrated. Shape: Ovate. Other: Moderately glossy, thick.

Disease resistance: Above average resistance to mildew, black spot, and Botrytis under normal growing conditions in Burlington, Canada.

Cold hardiness:

'POULush' has been found to be resistant to damage from cold, heat and drought damage in USDA Zone 7.

We claim:

1. A new and distinct variety of rose plant of the miniature class, substantially as herein illustrated and described as a distinct and novel rose variety due to its abundant flowers, vigorous and compact growth, year round flowering under glasshouse conditions, suitability for production from softwood cuttings in pots, and durable flowers and foliage which make the variety suitable for distribution in the floral industry.

* * * * *

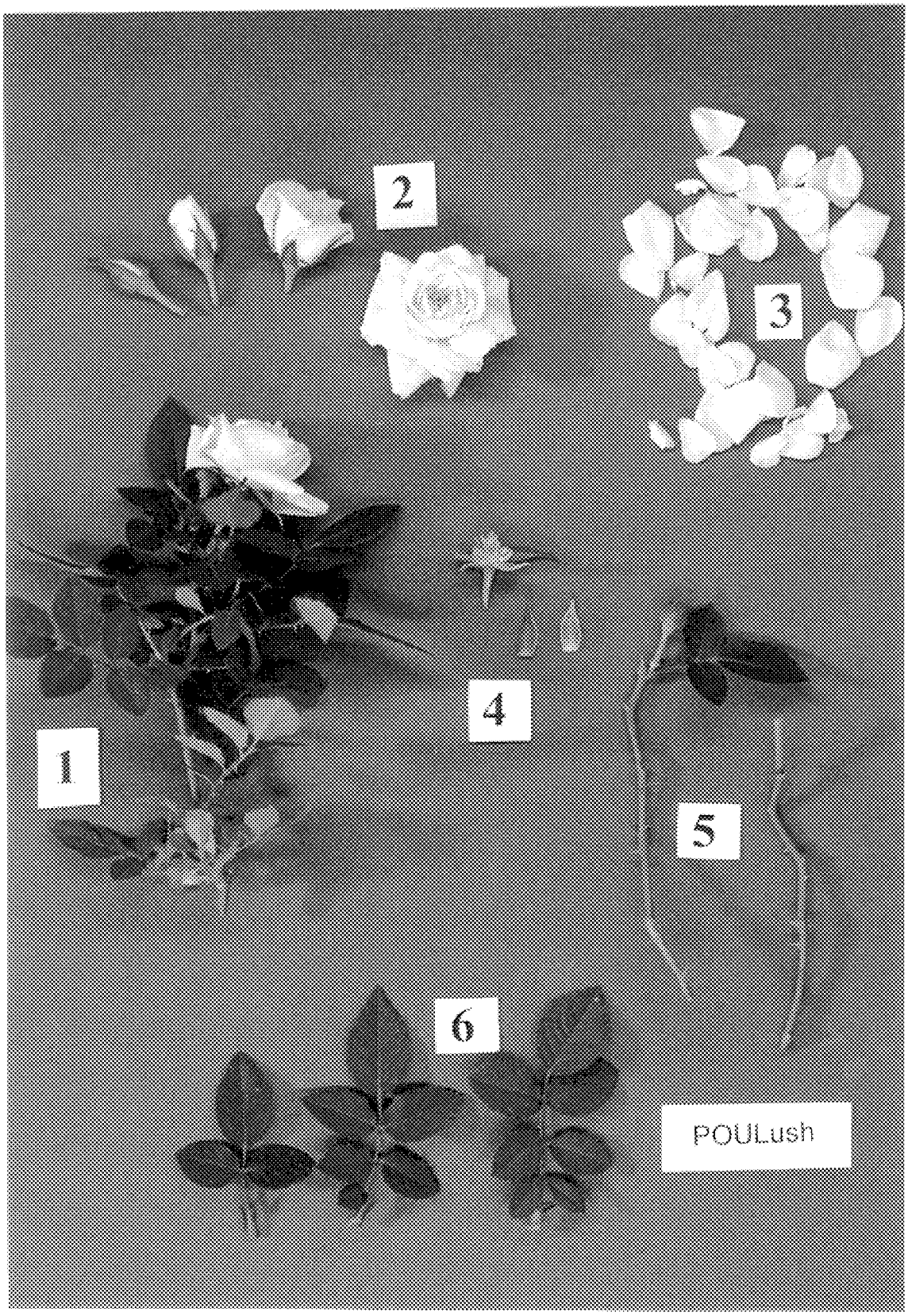
2
3
4
1
5
6
POULush